United States Patent
Zagorchev et al.

(10) Patent No.: US 11,288,803 B2
(45) Date of Patent: Mar. 29, 2022

(54) ABLATION RESULT VALIDATION SYSTEM

(71) Applicant: KONINKLIJKE PHILIPS N.V., Eindhoven (NL)

(72) Inventors: Lyubomir Georgiev Zagorchev, Burlington, MA (US); Joel Haaf, San Diego, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 393 days.

(21) Appl. No.: 16/152,577

(22) Filed: Oct. 5, 2018

(65) Prior Publication Data
US 2019/0108638 A1 Apr. 11, 2019

Related U.S. Application Data

(60) Provisional application No. 62/569,867, filed on Oct. 9, 2017.

(51) Int. Cl.
*G06T 7/00* (2017.01)
*G01R 33/48* (2006.01)
(Continued)

(52) U.S. Cl.
CPC .......... *G06T 7/0016* (2013.01); *A61B 5/0036* (2018.08); *A61B 5/0042* (2013.01);
(Continued)

(58) Field of Classification Search
CPC ..... A61B 5/055; A61B 5/0042; A61B 5/4848; A61B 5/0036; G01R 33/5608; G06T 7/0016
See application file for complete search history.

(56) References Cited

U.S. PATENT DOCUMENTS 9,220,458 B2 12/2015 Pouratian
9,256,951 B2 2/2016 Zagorchev
(Continued)

FOREIGN PATENT DOCUMENTS

WO WO-2012041364 A1 * 4/2012 ............ G06T 7/149
WO 2012125829 A2 9/2012
(Continued)

OTHER PUBLICATIONS

Mondal et al.: "Efficient computation of cross-sections from human brain model by geometric processing", Journal of Real-Time Image Processing vol. 15, Apr. 2015, p. 421-434 (Year: 2015).*
(Continued)

*Primary Examiner* — Jason M Ip
(74) *Attorney, Agent, or Firm* — Micah Shalom-Kesselman

(57) ABSTRACT

Devices, systems, methods for validating ablation results in a patient's brain are provided. In some embodiments, the method for validating ablation result in a patient's brain includes obtaining magnetic resonance (MR) data of the patient's brain, by use of a magnetic resonance imaging (MRI) device; obtaining first imaging data of the patient's brain, by use of the MRI device; extracting, by use of computing device in communication with the MRI device, first fiber tracts passing through an anatomy in the patient's brain based on the first imaging data; obtaining, by use of the MRI device, second imaging data of the patient's brain after ablation of the anatomy in the patient's brain has started; extracting second fiber tracts passing through the anatomy in the patient's brain based on the second imaging data; and outputting a graphical representation of a comparison between the first fiber tracts and the second fiber tracts.

18 Claims, 10 Drawing Sheets
(8 of 10 Drawing Sheet(s) Filed in Color)

(51) Int. Cl.
*G01R 33/56* (2006.01)
*A61B 5/055* (2006.01)
*A61B 5/00* (2006.01)
*A61B 18/00* (2006.01)
*G01R 33/563* (2006.01)

(52) U.S. Cl.
CPC ............ *A61B 5/055* (2013.01); *A61B 5/4848* (2013.01); *A61B 18/00* (2013.01); *G01R 33/4806* (2013.01); *G01R 33/5608* (2013.01); *G01R 33/56341* (2013.01); *A61B 2018/00446* (2013.01); *A61B 2018/00577* (2013.01); *A61B 2576/026* (2013.01); *G06T 2207/10092* (2013.01); *G06T 2207/30016* (2013.01); *G06T 2207/30096* (2013.01)

(56) References Cited

U.S. PATENT DOCUMENTS

| | | | |
|---|---|---|---|
| 9,568,580 B2 | 2/2017 | Dale | |
| 9,600,138 B2* | 3/2017 | Thomas | A61B 8/0808 |
| 2009/0171184 A1* | 7/2009 | Jenkins | A61B 5/7435 |
| | | | 600/411 |
| 2009/0232374 A1* | 9/2009 | Simon | G01R 33/56341 |
| | | | 382/131 |
| 2012/0093381 A1* | 4/2012 | Fan | G06T 7/143 |
| | | | 382/131 |
| 2012/0327075 A1* | 12/2012 | Zagorchev | G06T 7/0012 |
| | | | 345/419 |
| 2014/0003696 A1 | 1/2014 | Taghva | |
| 2015/0045675 A1* | 2/2015 | Chernomorsky | A61B 1/00094 |
| | | | 600/471 |
| 2015/0146951 A1 | 5/2015 | Zagorchev | |
| 2016/0005169 A1* | 1/2016 | Sela | G09B 23/30 |
| | | | 382/131 |
| 2016/0354155 A1* | 12/2016 | Hodges | A61B 34/25 |
| 2017/0035320 A1 | 2/2017 | Verma | |
| 2017/0076452 A1 | 3/2017 | Yui | |
| 2017/0215794 A1* | 8/2017 | Trudel | A61B 5/021 |

FOREIGN PATENT DOCUMENTS

WO WO2016058075 A1 4/2016
WO WO2017081302 A1 5/2017

OTHER PUBLICATIONS

Riordan, Margaret et al "Laser Induced Thermal Therapy (LITT)for Pediatric Brain Tumors: case-based review", Translational Pediatrics, Jul. 2014, pp. 229.
Hooi, Lim Liang et al "Preoperative and Postoperative Diffusion Tensor Imaging in Patients with Extra-Axial Lesions at the Frontal or Temporal Regions of the Brain and Their Correlations with Neuropsychological Outcomes", Journal of Biomedical Science and Engineering, vol. 9, No. 13, Jan. 2016, pp. 611-623.
Zagorchev, L. et al.,"Evaluation of Traumatic Brain Injury Patients Using a Shape-Constrained Deformable Model," in Multimodal Brain Image Analysis MBIA 2011, Lecture Notes in Computer Science, vol. 7012. Springer, Berlin, Heidelberg.

* cited by examiner

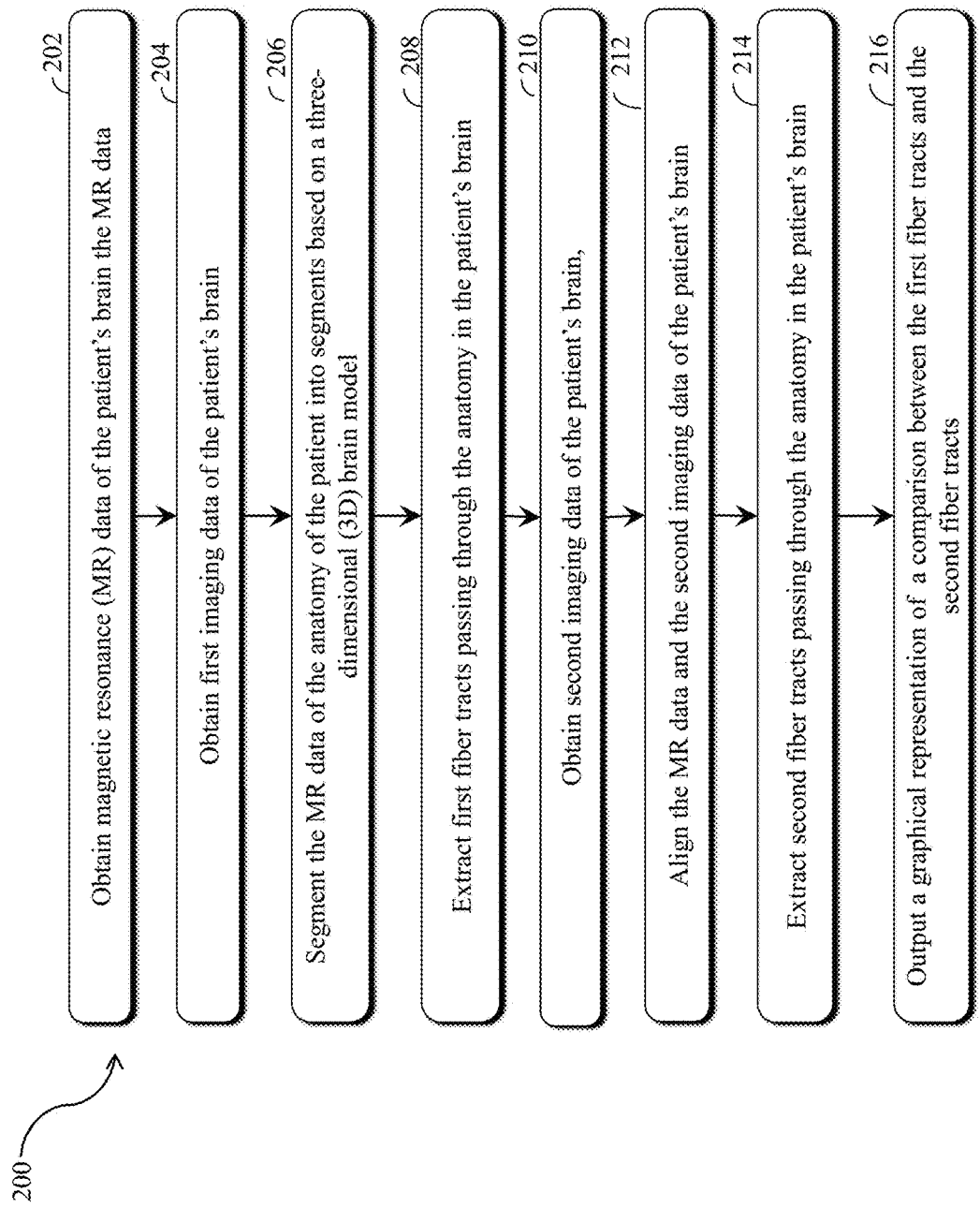

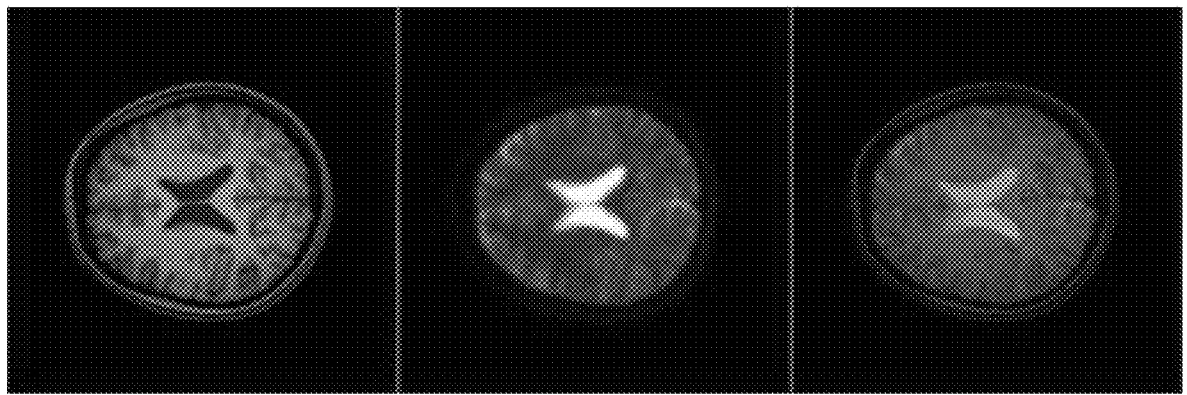

ABLATION RESULT VALIDATION SYSTEM

CROSS-REFERENCE TO RELATED APPLICATIONS

This patent application claims the priority benefit under 35 U.S.C. § 119(e) of U.S. Provisional Application No. 62/569,867 filed on Oct. 9, 2017, the contents of which are herein incorporated by reference.

TECHNICAL FIELD

The present disclosure relates generally to ablation result validation, and in particular, to devices, systems, and methods for validating ablation volumes and connectivity of an ablated target by visualizing the fiber tracts passing through the ablated target.

BACKGROUND

Minimally invasive intervention has increasingly been used to treat brain tumors and medically intractable epilepsy. One of emergent minimally invasive intervention techniques is interstitial thermal therapy (LITT). In a LITT procedure, an ablation catheter delivers heat to target cells by emitting collimated light through a diffusing tip, heating the target cells to 40° C. or higher. When heated to a temperature between 40° C. and 60° C., the target cells suffer irreversible cell damage due to denaturation of their DNA. Target cells heated to above 60° C. die instantly. When the target cells are heated to above 100° C., water in the target cells vaporizes and surrounding tissues carbonize.

The most common form of medically intractable epilepsy is mesial temporal lobe epilepsy (MTLE). Of the minimally invasive LITT procedures, stereotactic laser-guided amygdalohippocampectomy (SLAH) is used to treat MTLE. During a SLAH procedure, a craniotomy is performed to create a hole in a patient's skull. A polycarbonate anchor bolt is fixed to the hole, through which an alignment rod is driven into the patient's brain to create a path to the ablation target at or near the amygdalohippocampal complex (AHC) of the patient. Once the path is created, the alignment rod is removed and a polycarbonate cooling catheter with a diode laser fiber is inserted along the path to the ablation target.

The ablation process during a LITT procedure (such as the SLAH procedure) is monitored visually using magnetic resonance (MR) thermography overlaid on a pre-surgical T1 weighted magnetic resonance imaging (T1W MII) volume. Most clinical centers perform an additional T1W MII at the end of a LITT procedure to estimate the ablation volume. However, post-operative data overestimates the actual ablation due to changes in tissue contrast after the ablation. A major limitation of the current clinical workflow is the inability to detect and monitor the actual effect of ablation on target regions and functional integrity/connectivity (or reduction thereof) of ablated regions.

That major limitation takes a toll on the efficacy of the LITT procedures and can result in repeat ablations. Taking the treatment of intractable epilepsy as an example, the seizure freedom rate after a SLAH procedure varies from 40% to 60%, which is worse than that of the conventional open amygdalohippocampectomy procedure. This is disappointing because LITT is otherwise superior to conventional surgery as LITT substantially reduces non-target brain tissue brain damage, risk of complications, pain, discomfort, and permanent neurologic deficits. Among the MTLE patients who received a SLAH procedure, patients with epilepsy detectable by MRI are on the higher end of the range. Furthermore, the outcome depends on the amount of ablated AHC tissue. Approximately 80% of patients with ablation of at least 70% of either the amygdala or hippocampus and ablation of at least 50% of the other structure are seizure-free after the SLAH procedures. In contrast, only 40% of patients with ablation of less than 50% of the amygdala and hippocampus are seizure-free after the SLAH procedures. Some of these patients may consider or be advised of another LITT procedure to achieve seizure freedom. A means to more accurately quantify the extent of LITT ablation is desired to allow for more complete and effective ablation, increased seizure-free outcomes and to eliminate the need to subsequent repeated visits/ablations. While the foregoing is described with respect to treatment of the MTLE, the means to accurately quantify the extent of LITT ablation is equally desired to the LITT treatment of brain tumors and brain lesions.

SUMMARY

Embodiments of the present disclosure are configured to validating ablation result in a patient's brain by comparing intra- or post-ablation fiber tracts passing through the patient's anatomy with the pre-ablation fiber tracts passing through the patient's anatomy. The pre-ablation fiber tracts passing through the patient's anatomy are extracted based on imaging data, such as diffusion tensor imaging (DTI) data, obtained before the ablation. The intra- or post-ablation fiber tracts passing through the patient's anatomy are extracted based on imaging data, such as DTI data, obtained simultaneously with or after the ablation. The systems and methods disclosed in the present disclosure can also output a graphical representation of a comparison between the post-ablation fiber tracts and the pre-ablation fiber tracts. Aspects of the present disclosure advantageously provide a method and a system to accurately evaluate LITT ablation quantitatively to improve the efficacy of LITT and eliminate the need for subsequent repeat ablations.

In one embodiment, a method for validating an ablation result in a patient's brain is provided. The method includes obtaining magnetic resonance (MR) data of the patient's brain, by use of a magnetic resonance imaging (MRI) device; obtaining first imaging data of the patient's brain, by use of the MRI device; extracting, by use of computing device in communication with the MRI device, first fiber tracts passing through an anatomy in the patient's brain based on the first imaging data; obtaining, by use of the MRI device, second imaging data of the patient's brain after ablation of the anatomy in the patient's brain has started; extracting second fiber tracts passing through the anatomy in the patient's brain based on the second imaging data; and outputting a graphical representation of a comparison between the first fiber tracts and the second fiber tracts. In some embodiments, the first and second imaging data include diffusion tensor imaging (DTI) data.

In some embodiments, the second imaging data is obtained during the ablation of the anatomy in the patient's brain. In some other embodiments, the second imaging data is obtained after the ablation of the anatomy in the patient's brain has ended. In some implementations, outputting the graphical representation includes outputting to a display the second fiber tracts along with the MR data of the patient's brain. In some embodiments, the MR data includes T1 weighted magnetic resonance (T1W MR) data of the patient's brain. In some instances, the anatomy in the patient's brain can include an amygdalohippocampal complex, an amygdala, a hippocampus, a lesion, or a tumor in the patient's brain. In some embodiments, the extracting the second fiber tracts passing through the anatomy in the patient's brain based on the second imaging data includes aligning the MR data and the second imaging data of the patient's brain, wherein the MR data includes MR data of the anatomy in the patient's brain; segmenting the MR data of the anatomy in the patient's brain into segments based on a three-dimensional (3D) brain model; and identifying the second fiber tracts passing through the segments. In some implementations, the 3D brain model is a shape-constrained deformable brain model.

In another embodiment, a system for validating an ablation result in a patient's brain is provided. The method includes a computing device in communication with a magnetic resonance imaging (MRI) device, the computing device operable to obtain magnetic resonance (MR) data of the patient's brain, by use of a magnetic resonance imaging (MRI) device; obtain first imaging data of the patient's brain, by use of the MRI device; extract first fiber tracts passing through an anatomy in the patient's brain based on the first imaging data; obtain, by use of the MRI device, second imaging data of the patient's brain after ablation of the anatomy in the patient's brain has started; extract second fiber tracts passing through the anatomy in the patient's brain based on the second imaging data; and outputting, to a display in communication with the computing device, a graphical representation of a comparison between the first fiber tracts and the second fiber tracts. In some embodiments, the system for validating ablation result in a patient's brain further includes the MRI device and the display. In some embodiments, the first and second imaging data include diffusion tensor imaging (DTI) data.

In some embodiments, the computing device of the system for validating ablation result in a patient's brain is configured to obtain the second imaging data during the ablation of the anatomy in the patient's brain. In some other embodiments, the computing device is configured to obtain the second imaging data after the ablation of the anatomy in the patient's brain has ended. In some implementations, the computing device is configured to output to the display the second fiber tracts along with the MR data of the patient's brain. In some instances, the MR data includes T1 weighted magnetic resonance (T1W MR) data of the patient's brain. In some embodiments, the anatomy of in the patient's brain can include an amygdalohippocampal complex, an amygdala, a hippocampus, a lesion, or a tumor in the patient's brain. In some embodiments, the computing device of the system is further operable to align the MR data and the second imaging data of the patient's brain, wherein the MR data includes MR data of the anatomy in the patient's brain; segment the MR data of the anatomy in the patient's brain into segments based on a three-dimensional (3D) brain model; and identify the second fiber tracts passing through the segments. In some implementations, the 3D brain model is a shape-constrained deformable brain model.

Other devices, systems, and methods specifically configured to interface with such devices and/or implement such methods are also provided.

Additional aspects, features, and advantages of the present disclosure will become apparent from the following detailed description along with the drawings.

BRIEF DESCRIPTIONS OF THE DRAWINGS

The patent or application file contains at least one drawing executed in color. Copies of this patent or patent application publication with color drawing(s) will be provided by the Office upon request and payment of the necessary fee. Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 2 is a flowchart illustrating a method of validating ablation result in a patient's brain, according to aspects of the present disclosure.

FIG. 3A is an MR image of a patient's brain, according to aspects of the present disclosure.

FIG. 3B is a DTI image of a patient's brain, according to aspects of the present disclosure.

FIG. 3C shows a graphic representation of the MR image in FIG. 3A overlaid with the DTI image in FIG. 3B, according to aspects of the present disclosure.

DETAILED DESCRIPTION

Figure 1:
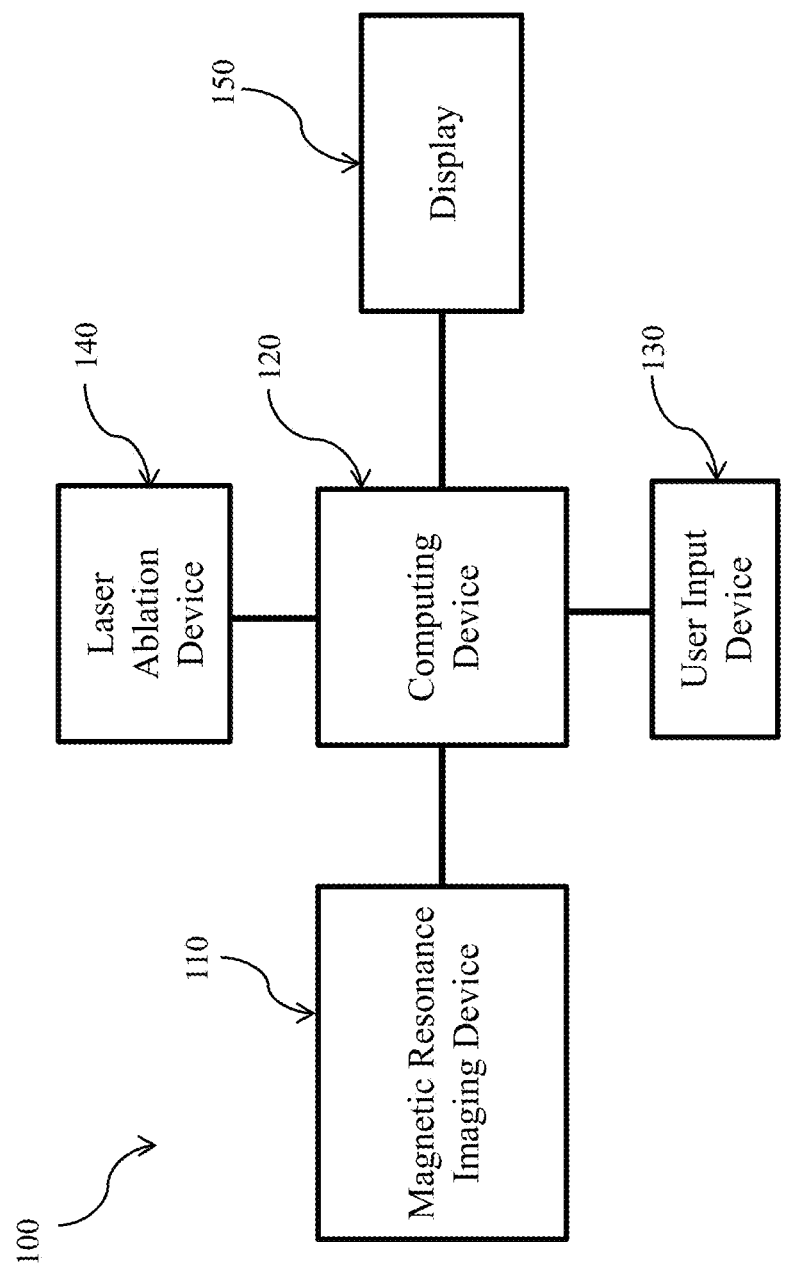
FIG. 1 is a schematic diagram of a system for validating ablation result in a patient's brain, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates.

Referring now to FIG. 1, shown therein is a schematic diagram of a system 100 for ablation result validation in a patient's brain. The system 100 includes a computing device 120 connected to a magnetic resonance imaging (MRI)

device 110, a user input device 130, a laser ablation device 140, and a display 150. The computing device 120 includes a processing circuit, such as one or more processors in communication with memory. The memory can be tangible computer readable storage media that stores instructions that are executable by the one or more processors. The computing device 120 can be a workstation or a controller that serves as an interface between the MRI device 110 and the laser ablation device 140. In some embodiments, the MRI device 110 can operate in different modalities, including but not limited to magnetic resonance (MR) imaging, diffusion tensor imaging (DTI), and positron emission tomography (PET) imaging and output imaging data to the computing device 120. In some implementations, the MRI device 110 can operate in different modalities at the same time. For example, in some embodiments of the present disclosure, the MRI device can perform MR scans and PET scans simultaneously or MR scans and DTI scans simultaneously. DTI utilizes the properties of water diffusion to provide information about connectivity and function integrity of brain tissues. It is based on the principle that water molecules diffuse along the principal axes of tensors that describe the rate of diffusion. The tensors are centered at voxels in three dimensions and can be visualized as ellipsoids. As a result, voxels along common fiber pathways form "diffusion lines," also known as fiber tracts, if viewed along the long axes of their individual tensors. DTI or DTI tractography is an image processing technique that traces such ellipsoids along their long axis by starting from a user-defined seed point/region.

In some embodiments, the computing device 120 can receive MR data from the MRI device 110, process the same and output MR image data to the display 150 such that the display 150 can display MR images. In some embodiments, the computing device 120 can receive DTI data from the MRI device 110, extract fiber tracts passing through an anatomy of a patient, and output image data of the fiber tracts to the display 150. In some implementations where the MR data and the DTI data are obtained simultaneously by the MRI device 110, no co-registration or alignment may be necessary as both data may already be aligned. In some implementations where the MR data and the DTI data are not obtained simultaneously or are obtained simultaneously, the computing device 120 can align or co-register the MR data and the DTI data through rigid registration, volume localization or direction cosines. In either case, the computing device 120 can process aligned MR data and DTI data and output MR image data overlaid with DTI data. The same applies to PET data obtained by the MRI device 110. If the MR data and PET data from the MRI device 110 are obtained simultaneously, no co-registration or alignment may be necessary. However, if the MR data and PET data from the MRI device 110 are obtained sequentially or simultaneously in some instances, the imaging data can be aligned through any suitable process, such as rigid registration, volume localization, direction cosines, etc.

In an embodiment, the laser ablation device 140 includes an MRI-compatible ablation catheter (ablation catheter) and a catheter driver. The catheter driver can drive the ablation catheter into a patient's skull through a hole created in a craniotomy procedure. The user input device 130 serves as an interface between a user and the computing device 120 and allows the user to interact with the computing device 120 by entering user inputs. The user input device 130 can be a keyboard, a mouse, a touchpad, a track pad, a touchscreen mounted on the display 150, a hand gesture control device, or a virtual reality glove. The MRI-compatible ablation catheter of the laser ablation device 140 allows MR image of the patient's brain to be obtained by the MRI device 110 in real time during a LITT procedure. The real-time MR images of the patient's brain provide visualization and guidance to the surgeon that performs the LITT procedure.

In some embodiments, the system 100 can be used to validate ablation result in MRI-guided LITT procedures by comparing the pre-ablation fiber tracts passing through a target brain anatomy with the intra- or post-ablation fiber tracts passing through the target brain anatomy. To obtain the pre-ablation fiber tracts, MR data and a non-MR imaging data of a patient's brain is obtained by the MRI device 110 before the LITT procedure. As used herein, the non-MR imaging data refer to data that are not MR data or are of a different modality from the MR data. Non-MR imaging data can be used to identify fiber tracts of a patient's brain. The non-MR imaging data can be obtained by the MRI device 110 or another medical imaging device. An example of non-MR imaging data is DTI data. Non-MR imaging data can include other suitable imaging data, such as PET data. It is noted that while the embodiments of the present disclosure are described in conjunction with DTI data as the non-MR imaging data, other non-MR imaging data are also envisioned. Moreover, while MRI device 110, MR data, and DTI imaging data are specifically mentioned in the some embodiments, in other embodiments, any suitable imaging data can be utilized for one or more operations of the method 200, described below, such as operations 202, 204, and/or 210. For example, the imaging data can be PET data, computed tomography (CT) data, radiographic data, x-ray data, MR data, DTI data, etc. In instances where the MR data and the non-MR imaging data are not obtained simultaneously, the MR data is aligned or co-registered with the non-MR imaging data by the computing device 120 through rigid registration, volume localization or direction cosines.

In order to extract fiber tracts passing through the target brain anatomy, the boundary of the target brain anatomy in the MR image is segmented into segments or regions by the computing device 120 based on a three-dimensional (3D) brain model. In some instances, the 3D brain model is received by the computing device 120 from a storage media or through wired or wireless connection to a server or a remote workstation. In some other instances, the 3D brain model can be stored in a storage device in the computing device 120 or a storage device retrievable by the computing device 120. In some implementations, the 3D brain model is a shape-constrained deformable brain model. In some instances, the 3D brain model may be the brain model described in "Evaluation of traumatic brain injury patients using a shape-constrained deformable model," by L. Zagorchev, C. Meyer, T. Stehle, R. Kneser, S. Young and J. Weese, 2011, in *Multimodal Brain Image Analysis* by Liu T., Shen D., Ibanez L., Tao X. (eds). MBIA 2011. *Lecture Notes in Computer Science*, vol. 7012. Springer, Berlin, Heidelberg, the entirety of which is hereby incorporated by reference. In some embodiments, the 3D brain model may be the deformable brain model described in U.S. Pat. No. 9,256,951, titled "SYSTEM FOR RAPID AND ACCURATE QUANTITATIVE ASSESSMENT OF TRAUMATIC BRAIN INJURY" or the shape-constrained deformable brain model described in U.S. Pat. App. Pub. No. 20150146951, titled "METHOD AND SYSTEM FOR QUANTITATIVE EVALUATION OF IMAGE SEGMENTATION," each of which is hereby incorporated by reference in its entirety.

With the MR data and the DTI data aligned, the segments of the target brain anatomy can be transferred to the DTI space. By utilizing the segments and regions as the seed regions or starting regions in the DTI space, the computing device 120 can extract from the DTI data pre-ablation fiber tracts that pass through the segments or regions. As these fiber tracts represent neurons that run through the target brain anatomy, the pre-ablation fiber tracts represent the functional integrity and connectivity of the target brain anatomy before ablation. For the ease of reference, the pre-ablation DTI data can be referred to as first DTI data and the pre-ablation fiber tracts can be referred to as first fiber tracts. The image data of these pre-ablation fiber tracts can be output to the display 150 for display and stored in a storage device in the computing device 120 or a storage device retrievable by the computing device 120. In some embodiments, the pre-ablation fiber tracts can be displayed along with the MR image of the patient's brain to aid a surgeon in planning an optimal ablation trajectory through the patient's brain so as to ensure sufficient ablation of the target brain anatomy while keeping non-target brain tissue brain damage, risk of complications, pain, discomfort, and permanent neurologic deficits at a low level.

In some embodiments, the laser ablation device 140 can be utilized to ablate the target brain anatomy. The ablation can remove or vaporize brain tissues at or near the target brain anatomy, creating void in the patient's brain or disrupting the fiber tracts passing through the target brain anatomy. In theory, if the entire target brain anatomy is removed by ablation, the portion of fiber tracts contained within the volume of the target brain anatomy should disappear. During or after ablation of the target brain anatomy, DTI data of patient's brain is obtained again. If the DTI data of the patient's brain is obtained during the ablation of the target brain anatomy, the fiber tracts extracted from such DTI data can be referred to as intra-ablation fiber tracts. If the DTI data of the patient's brain is obtained after the ablation of the target brain anatomy, the fiber tracts extracted from such DTI data can be referred to as post-ablation fiber tracts. For the ease of reference, the intra- or post-ablation fiber tracts can be referred to as second fiber tracts. Similarly, the DTI data obtained during or after the ablation is referred to as the intra- or post-ablation DTI data or second DTI data. Because the second ablation DTI data is not simultaneously obtained with the MR data, the computing device 120 is to align or co-register the MR data and the second DTI data by rigid registration, volume localization, or direction cosines. The computing device 120 can extract from the second DTI data the second fiber tracts that pass through the segments or regions. In some embodiments, the computing device 120 can compare the first fiber tracts and the second fiber tracts and output a graphical representation of the comparison to the display 150. This graphical representation allows the surgeons to validate the efficacy of the ablation by visualizing the reduction of functional integrity and connectivity of the target brain anatomy. In some implementations, the computing device 120 can quantitatively compare the number, density or volume of the pre-ablation fiber tracts and that of the post-ablation fiber facts and the graphical representation can be a percentage of reduction in number, density or volume.

Referring now to FIG. 2, shown therein is a flowchart illustrating am exemplary method 200 of validating ablation result in a patient's brain. The method 200 includes operations 202, 204, 206, 208, 210, 212, 214, and 216. It is understood that the operations of method 200 may be performed in a different order than shown in FIG. 2, additional operations can be provided before, during, and after the operations, and/or some of the operations described can be replaced or eliminated in other embodiments. The operations of the method 200 can be carried out by a computing device in an ablation trajectory planning system, such as the computing device 120 of the system 100. The method 200 will be described below with reference to FIGS. 3A, 3B, 3C, 3D, 4, 5, 6A, 6B, 7, and 8.

At operation 202 of the method 200, MR data of the patient's brain is obtained by use of the MRI device 110 in communication with the computing device 120. The computing device 120 can process the MR data of a patient's brain and output MR image data to the display 150 to display an MR image 300 shown in FIG. 3A. In some embodiments, the MR data includes T1 weighted magnetic resonance (T1W MR) data. While the MR image 300 shown in FIG. 3A is a top view of the patient's brain. A person of ordinary skill in the art would understand that MR images of the patient's brain from other views can be obtained or derived by the computing device 120 as well. The MR data obtained at operation 202 includes MR data of anatomies in the patient's brain, including the MR data of a target brain anatomy (sometimes referred to as the anatomy) in the patient's brain.

Figure 3D:
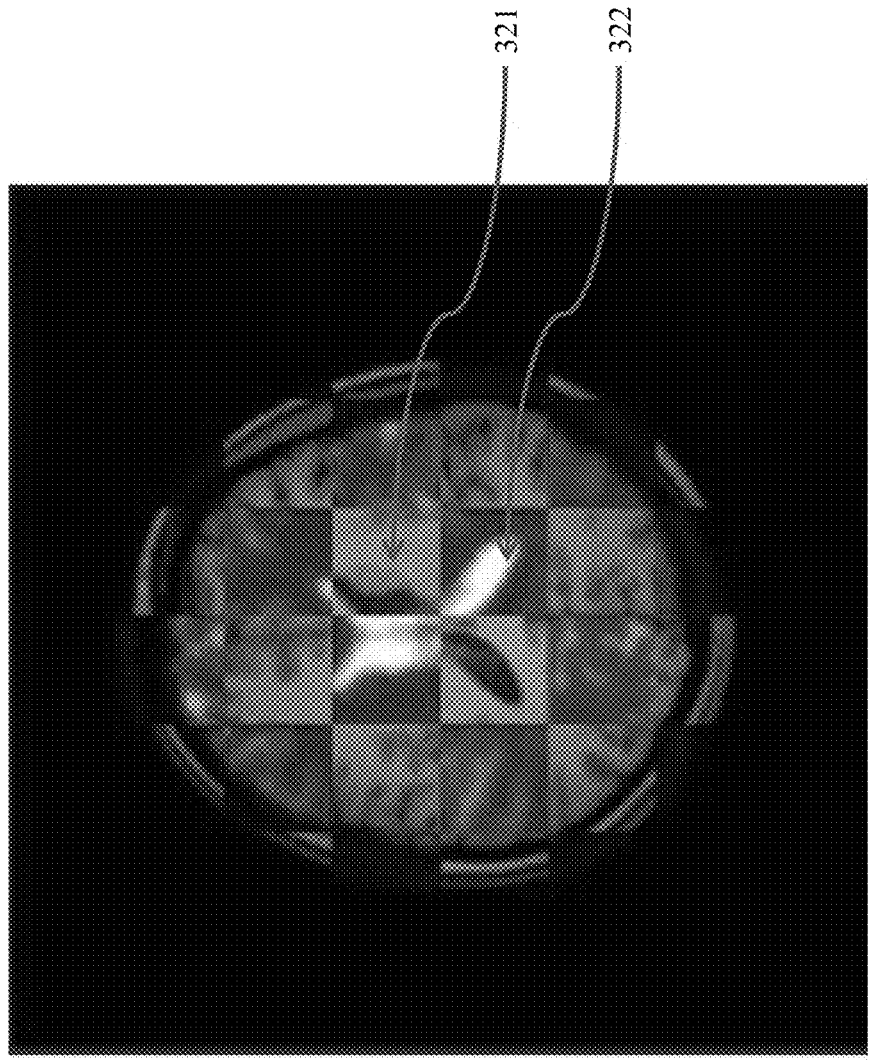
FIG. 3D shows another graphic representation of the MR image in FIG. 3A overlaid with the DTI image in FIG. 3B, according to aspects of the present disclosure.

At operation 204 of the method 200, first imaging data of the patient's brain is obtained by use of the MRI device 110 in communication with the computing device 120. In some embodiments represented by FIGS. 3B, 3C and 3D and to be described in details below, the first imaging data include first DTI data. In those embodiments, the first imaging data can be referred to as the first DTI data. However, it is noted that, in some alternative embodiments, the first imaging data can include PET data, computed tomography (CT) data, radiographic data, and x-ray data that are obtained by use of the MRI device 110 or another medical imaging device. In some embodiments, the operation 204 can take place before, after or simultaneously with the operation 202. Because the first DTI data of the patient's brain is obtained before a LITT ablation using the laser ablation device 140, the first DTI data can also be referred to as the pre-ablation DTI data. The computing device 120 can receive the first DTI data from the MRI device 110 and output first DTI image data to the display 150 to display a DTI image 310 in FIG. 3B. Like FIG. 3A, which is a top view of the patient's brain, FIG. 3B is also a top view of the patient's brain. A person of ordinary skill in the art would understand that pre-ablation DTI images of the patient's brain from other views can be obtained or derived by the computing device 120 based on the first DTI data.

In embodiments where operations 202 and 204 take place simultaneously by use of the MRI device 110, alignment or co-registration between the MR data obtained in operation 202 and the first DTI data obtained in operation 204 is not necessary as both data are automatically aligned. However, if operations 202 and 204 are not carried out simultaneously, the MR data are to be aligned or co-registered with the first DTI data through rigid registration, volume localization or direction cosines. FIGS. 3C and 3D show different representation of the aligned MR data and first DTI data. FIG. 3C demonstrates MR image data overlaid with the DTI image data and the resulting image 320 is a superposition overlay of the MR image 300 and the DTI image 310. FIG. 3D is a compartmented view of the overlay of the MR image 300 and DTI image 310, showing both MR image compartments like compartment 321 and DTI image compartments like compartment 322. The alternative representation in FIG. 3D shows how the boundaries of brain anatomies in the MR image 300 are aligned/co-registered with those in the DTI image 310.

Figure 4:
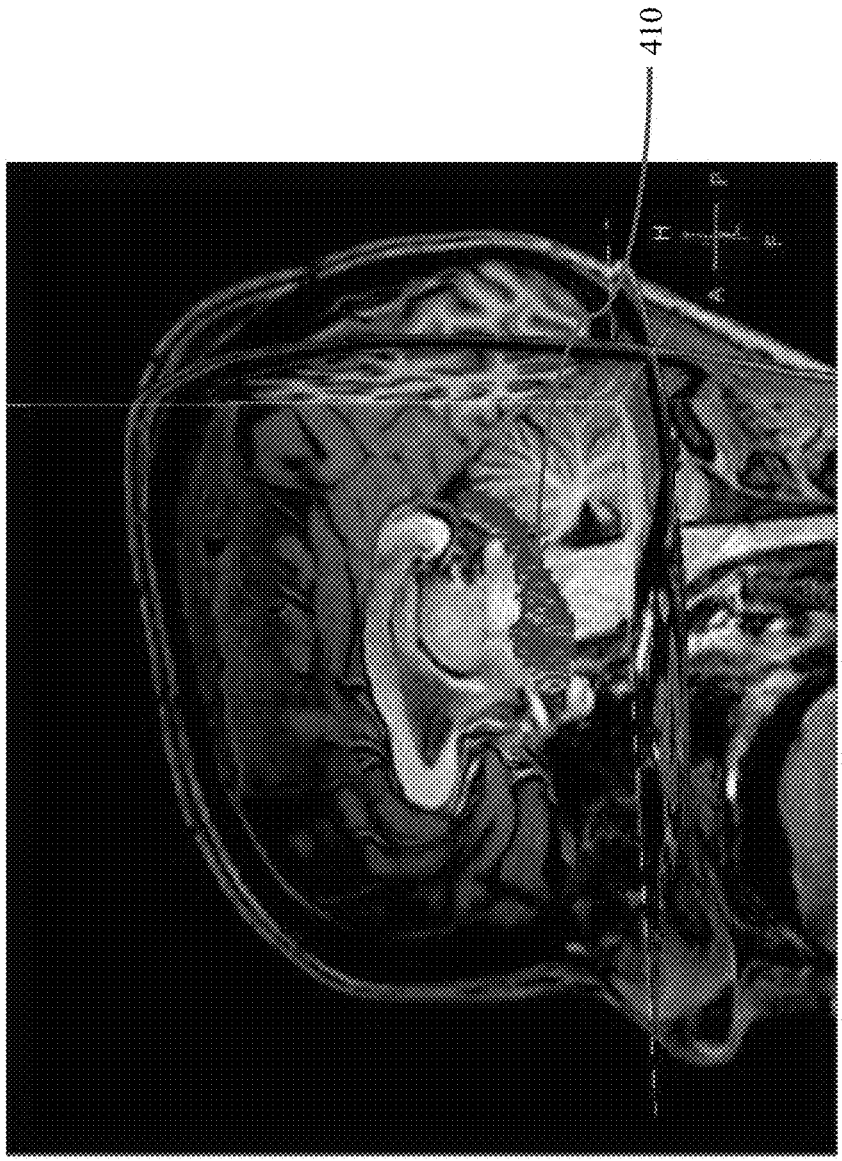
FIG. 4 is an MR image of a patient's brain overlaid with a segmented model of the patient's AHC, according to aspects of the present disclosure.

At operation 206 of the method 200, the MR data of the anatomy of the patient are segmented into segments or regions based on a 3D brain model. In some embodiments, the 3D brain model is a shape-constrained deformable brain model. In some instances, the 3D brain model may be the brain model described in "Evaluation of traumatic brain injury patients using a shape-constrained deformable model," by L. Zagorchev, C. Meyer, T. Stehle, R. Kneser, S. Young and J. Weese, 2011, in *Multimodal Brain Image Analysis* by Liu T., Shen D., Ibanez L., Tao X. (eds). MBIA 2011. *Lecture Notes in Computer Science*, vol. 7012. Springer, Berlin, Heidelberg, the entirety of which is hereby incorporated by reference, in some instances, the 3D brain model may be the deformable brain model described in U.S. Pat. No. 9,256,951 titled "SYSTEM FOR RAPID AND ACCURATE QUANTITATIVE ASSESSMENT OF TRAUMATIC BRAIN INJURY" or the shape-constrained deformable brain model described in U.S. Pat. App. Pub. No. 20150146951, titled "METHOD AND SYSTEM FOR QUANTITATIVE EVALUATION OF IMAGE SEGMENTATION," each of which is hereby incorporated by reference in its entirety. In some implementations, the 3D brain model is stored in the computing device 120 or a storage device or medium retrievable by the computing device 120. In some embodiments, the 3D brain model is formed of a surface mesh that includes a plurality of triangularly shaped polygons, each of which includes three vertices and edges. In some other embodiments, the 3D brain model may be formed of polygons of other shapes. The 3D brain model may be used to delineate the boundaries of anatomies in the patient's brain, including the boundaries of the target brain anatomy, for example, an AHC, an amygdala, a hippocampus, a brain tumor, or a brain lesion. One of the ways the 3D brain model delineates the boundary of an anatomy is by representing the anatomy in segments or regions. Such segmentation is demonstrated by FIG. 4, where an MR image 400 of the patient includes a segmented representation 410 of the patient's AHC. As shown in FIG. 4, the segmented representation 410 includes several plate-like segments/regions that track the boundary of the patient's AHC. While FIG. 4 shows the segmented representation 410 of the patient's AHC, people of ordinary skill in the art would understand that such segmentation can be done to all brain anatomies, including an AHC, an amygdala, a hippocampus, a brain tumor, or a brain lesion. In some implementations, the segmentation in operation 208 can be automatically carried out by the computing device 120 based on the 3D brain model without intervention of a user (e.g. a surgeon or a nurse), saving time and reducing variability introduced by different users.

Figure 5:
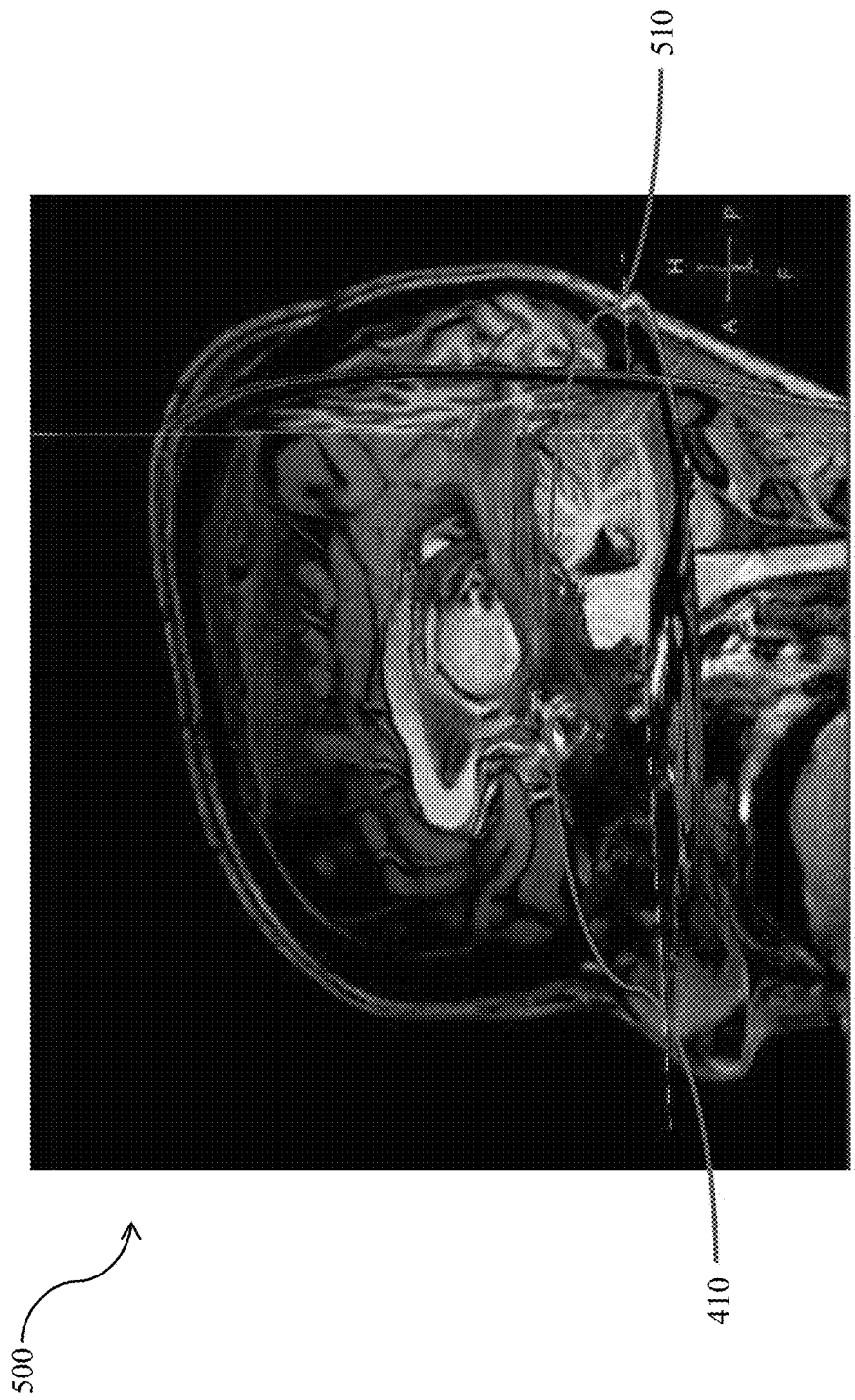
FIG. 5 is an MR image of a patient's brain overlaid with fiber tracts passing through the segmented model of the patient's AHC, according to aspects of the present disclosure.
Figure 6A:
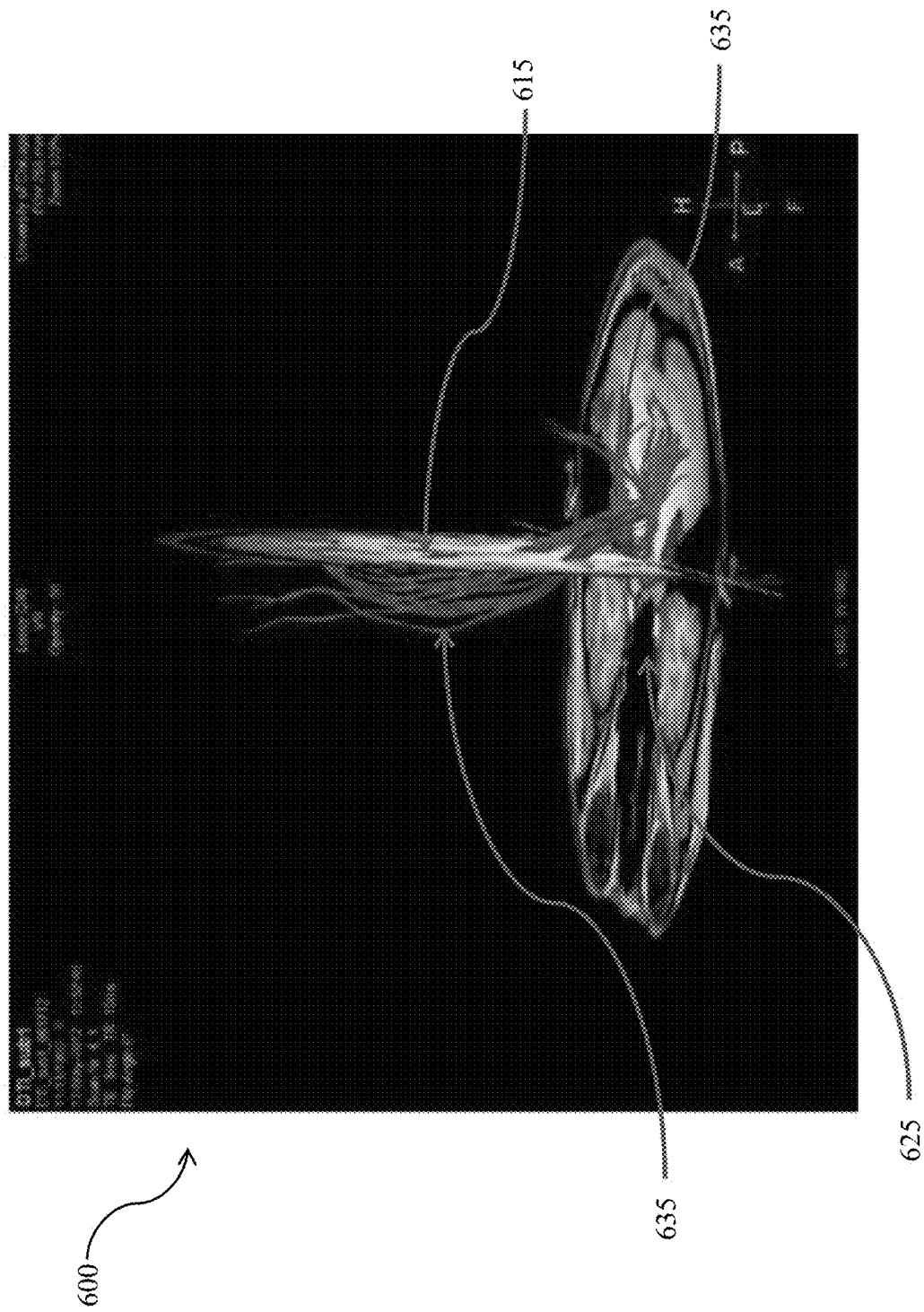
FIG. 6A is an MR image showing fiber tracts passing through seed planes, according to aspects of the present disclosure.
Figure 6B:
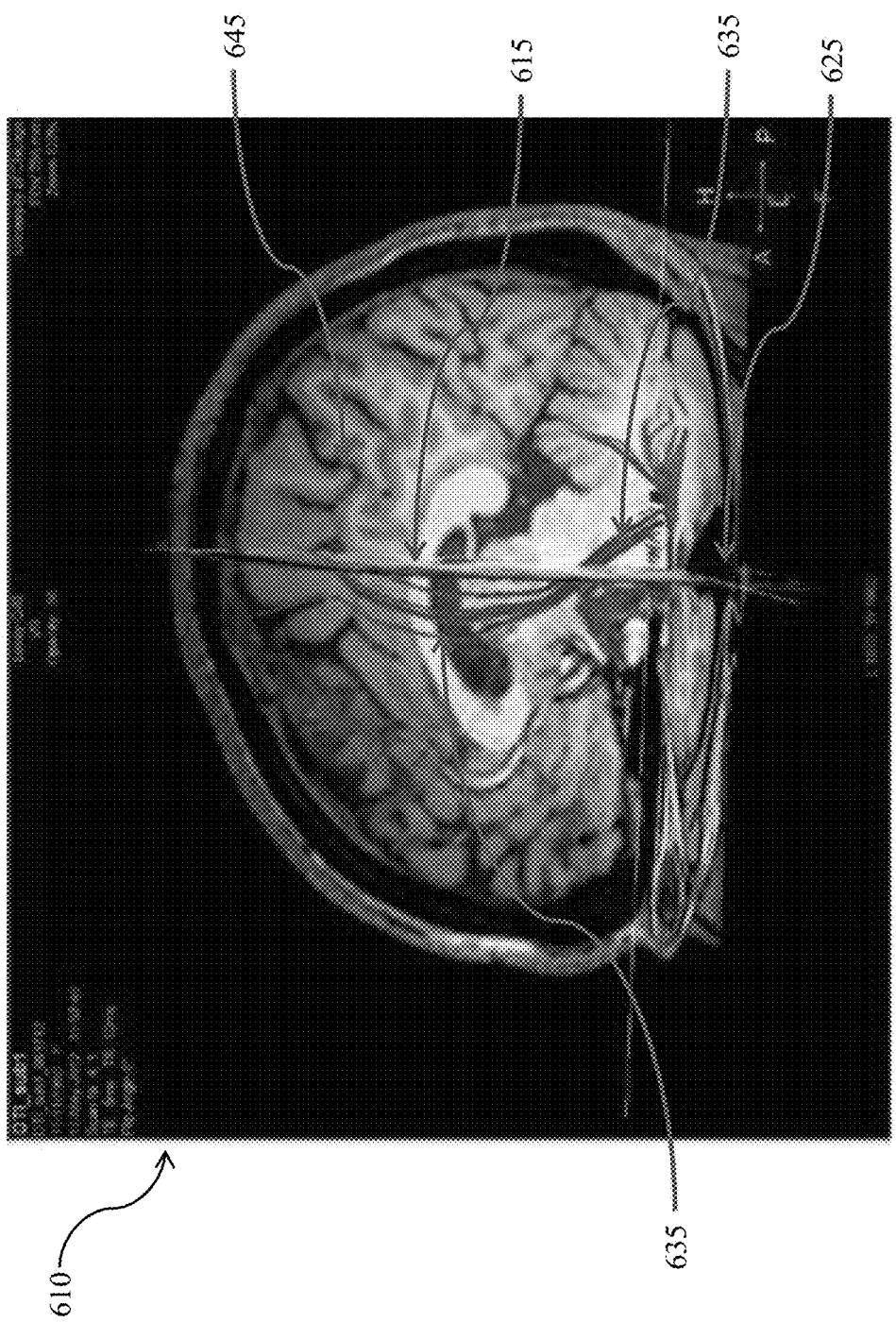
FIG. 6B is an MR image showing fiber tracts extracted from DTI data, according to aspects of the present disclosure.

Referring now to FIG. 5, shown therein is an MR image 500 of the patient's brain overlaid with fiber tracts 510 passing through the segmented representation 410 of the patient's AHC. At operation 208 of the method 200, fiber tracts 510 passing through the patient's AHC are extracted. In some embodiments, the plate-like segments/regions in the segmented representation 410 can serve as the starting point or "seed" to track the fiber tracts 510 passing through them, allowing the fiber tracts 510 to be extracted at operation 208. Because the fiber tracts 510 are extracted before ablation of the patient's AHC, the fiber tracts 510 can also be referred to as pre-ablation fiber tracts 510 or first fiber tracts 510. The process to track and extract first fiber tracts from first DTI data can be further explained by reference to FIGS. 6A and 6B. FIG. 6A is an MR image 600 showing fiber tracts 635 that pass through the segment 615 and segment 625. In the example shown in FIG. 6A, both segments 615 and 625 are set as the starting point to track fiber tracts. As a result, the extracted fiber tracts 635 pass through both the segment 615 and the segment 625. In some embodiments, to help a surgeon to visualize the distribution of the fiber tracts in a patient's brain, an MR image 645 of the patient's brain is also displayed along with the fiber tracts 635 and seed segments 615 and 625, as shown in the MR image 610 in FIG. 6B.

Figure 7:
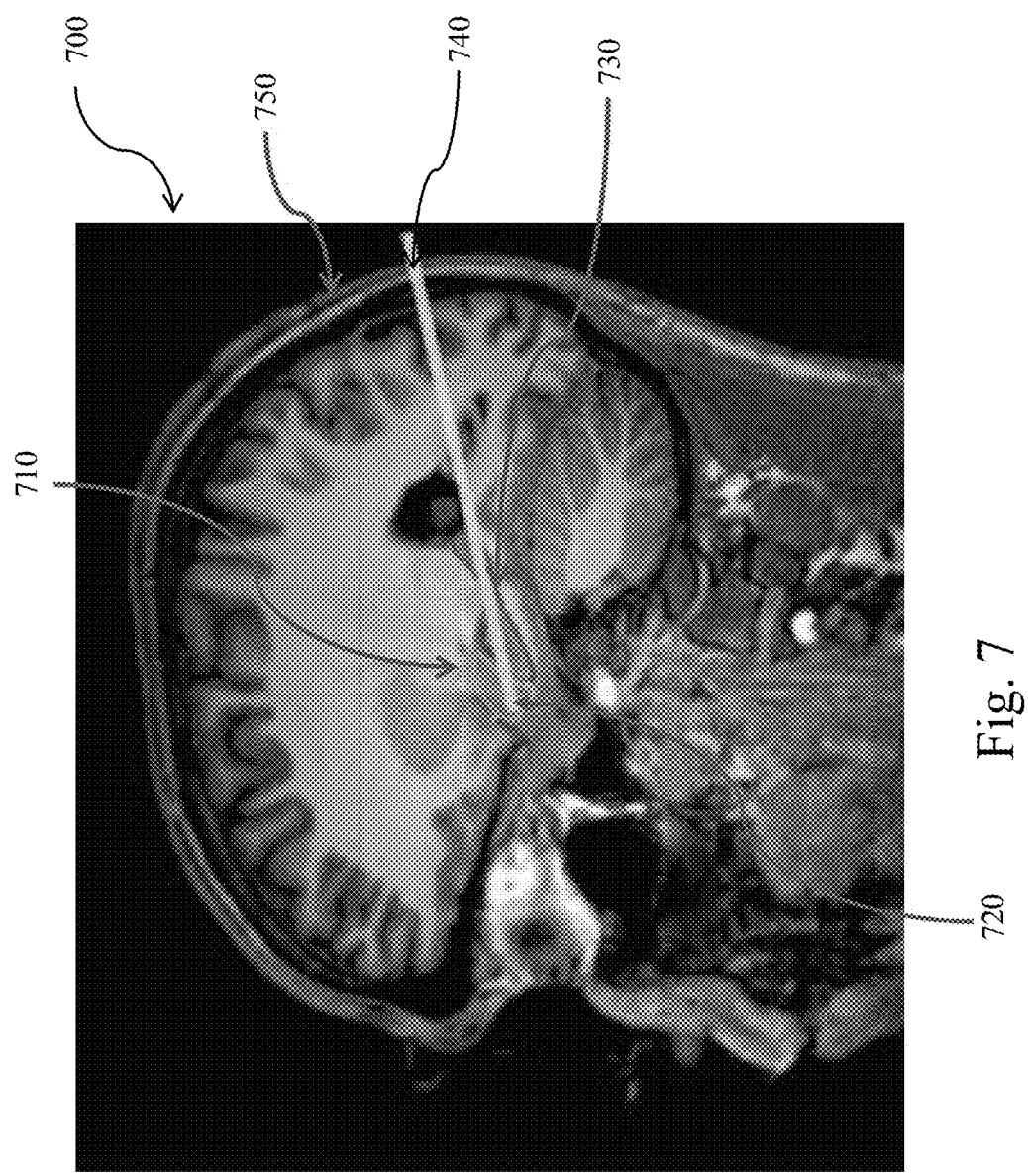
FIG. 7 is an MR image of a patient's brain showing the patient's AHC and a trajectory of a LITT ablation catheter, according to aspects of the present disclosure.

At operation 210 of the method 200, second imaging data of the patient's brain is obtained. In some embodiments to be described in details below, the second imaging data include second DTI data. In those embodiments, the second imaging data can be referred to as the second DTI data. However, it is noted that, in some alternative embodiments, the second imaging data can include other suitable imaging data obtained by use of the MRI device 110 or another medical imaging device. In some embodiments, operation 210 takes place simultaneously with or during ablation of the anatomy in the patient's brain (such as the patient's AHC) using the laser ablation device 140. In those embodiments, the second DTI data obtained can be referred to as intra-ablation DTI data. In some other embodiments, operation 210 takes place after ablation of the anatomy in the patient's brain. In those embodiments, the second DTI data may be referred to as the post-ablation DTI data. For the ease of reference, the intra- or post-ablation DTI data can be referred to as the second DTI data. Reference is now made to FIG. 7. As shown in the MR image 700, during the ablation, an ablation catheter of the laser ablation device 140 is inserted through the patient's skull 750 along a planned trajectory 740 to ablate the patient's AHC 710, which includes the patient's amygdala 720 and hippocampus 730. The ablation catheter can heat brain tissue in contact therewith to 40° C. or higher to damage, kill or vaporize them. In some instances, the ablation can sever, damage, or disrupt neurons going through the patient's AHC. In some other instances, the ablation can leave a void in the target brain anatomy, such as the patient's AHC in this example.

At operation 212 of the method 200, the MR data obtained in the operation 202 is aligned or co-registered with the second DTI data (intra- or post-ablation DTI data) obtained in the operation 210. In embodiments of the present disclosure, MR data and DTI data that are not obtained simultaneously need to be aligned or co-registered in order for a segmented representation of a brain anatomy to be transferred to the DTI space to serve as the seed for extraction. In embodiments represented by the flow chart in FIG. 2, the second DTI data is obtained after the ablation and is not obtained simultaneously with the MR data. Therefore, the second DTI data is to be aligned or co-registered with the MR data through rigid registration, volume localization or direction cosines at operation 212.

Figure 8:
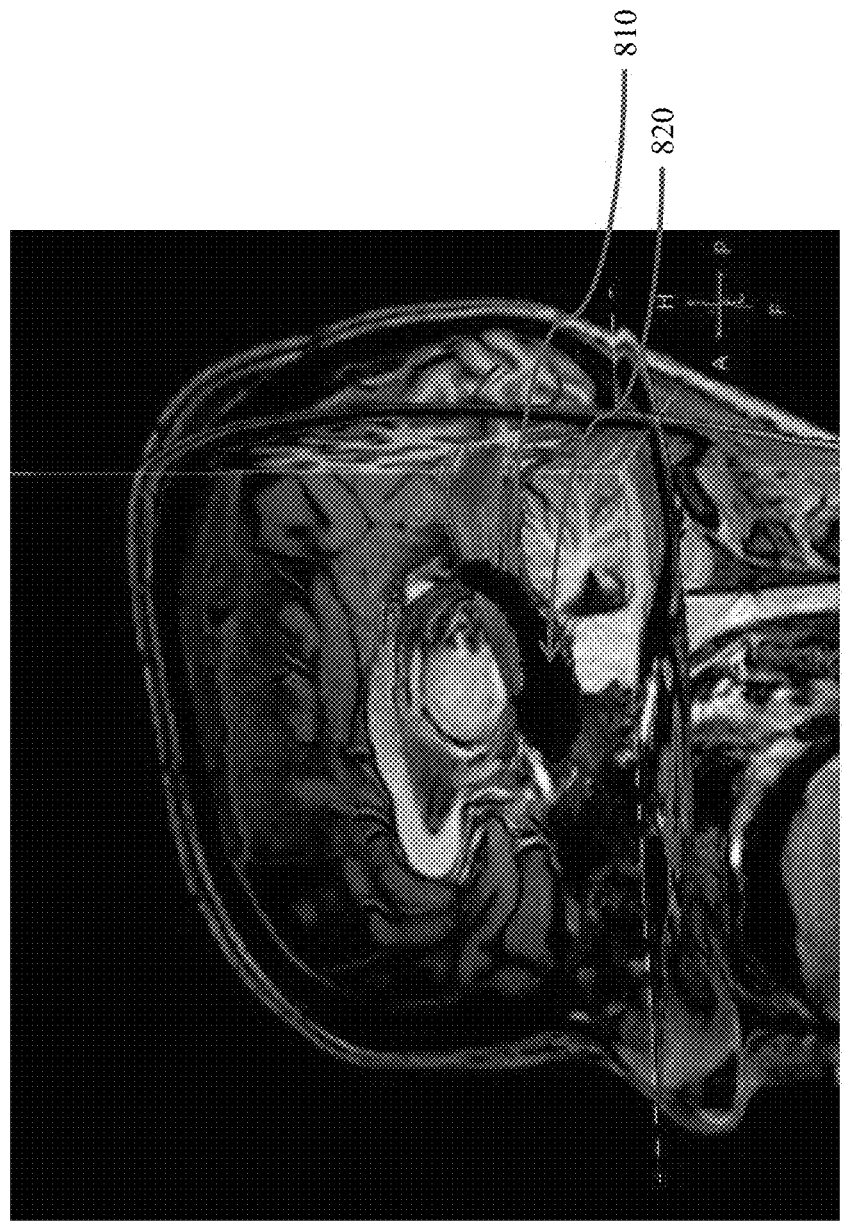
FIG. 8 is an MR image of a patient's brain overlaid with post-ablation fiber tracts passing through the segmented model of the patient's AHC, according to aspects of the present disclosure.

Reference is now made to the MR image 800 in FIG. 8. At operation 214 of the method 200, second fiber tracts 810 passing through the patient's AHC are extracted. Because the second fiber tracts 810 can be extracted during or after the ablation, the second fiber tracts 810 may sometimes be referred to as the intra- or post-ablation fiber tracts 810. As shown in FIG. 8, the ablation by use of the ablation catheter of the laser ablation device 140 severs and disrupts several fiber tracts that pass through the patient's AHC, leaving a void 820, where diffusion of water molecules is disrupted or restricted.

At operation 216 of the method 200, the computing device 120 compares the second fiber tracts 810 to the first fiber tracts 510 and outputs a graphical representation of the comparison between the second fiber tracts 810 and the first fiber tracts to the display 150. In some embodiments, the graphical representation may be the first fiber tracts 510 overlaid with the second fiber tracts 810. In some embodiments, the first fiber tracts 510 and the second fiber tracts 810 are displayed simultaneously but are assigned with different or contrasting colors. In some implementations, the computing device 120 can quantitatively compare the number of the first fiber tracts 510 and the number of the second fiber tracts 810 and output a percentage of reduction in the number of fiber tracts. In some other implementations, the computing device 120 can compare the volume occupied by the first fiber tracts 510 and the volume occupied by the second fiber tracts 810 and output a percentage of decrease in fiber tracts-occupied volumes. As these first and second fiber tracts 510 and 810 represent neurons that go through the patient's AHC, the graphical representation of their comparison can indicate the reduction of functional integrity and connectivity of the patient's AHC brought about by the ablation. This way, the method 200 disclosed in the present disclosure advantageously provides a method to assess and validate the ablation result as soon as the ablation is completed. The graphical representation can include a visual representation, a numerical representation, and/or a combination thereof.

If the ablation result is not satisfactory, the surgeon can immediately perform further ablation procedures in the same LITT operation until the ablation result is satisfactory. In some embodiments, the computing device 120 may compare the ablation result to normative or statistical data to determine if the ablation result is satisfactory. Taking SLAH for example, the clinical statistics reveals that 80% of patients with ablation of at least 70% of either the amygdala or hippocampus and ablation of at least 50% of the other structure are seizure-free after the SLAH procedures. If the comparison of the second fiber tracts to the first fiber tracts indicates that more than 30% of the connectivity of the patient's AHC remains. The computing device 120 may determine that less than 70% of the AHC is ablated and suggest further ablation.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A computer-implemented method for validating an ablation result in a patient's brain, the method comprising:
 receiving magnetic resonance (MR) data of the patient's brain;
 receiving first imaging data of the patient's brain;
 generating a segmented model of the patient's brain from the MR data, based on a 3D shape constrained deformable brain model adapted to the patient's brain, the 3D shape constrained deformable brain model comprising plate-like segments corresponding to boundaries of anatomy of the patient's brain;
 tracking, based on the first imaging data and the MR data, first fiber tracts passing through an anatomy in the patient's brain, wherein one of the plate-like segments of the segmented model of the patient's brain seeds the tracking of the first fiber tracts;
 receiving, from a MRI device, second imaging data of the patient's brain after ablation of the anatomy in the patient's brain has started;
 tracking, based on the second imaging data and the MR data, second fiber tracts passing through the anatomy in the patient's brain, wherein the segment of the segmented model of the patient's brain seeds the tracking of the second fiber tracts;
 determining a percentage decrease based on a comparison of one of (i) a first number of the first fiber tracts and a second number of the second fiber tract or (ii) a first volume occupied by the first fiber tracts and a second volume occupied by the second fiber tracts;
 validating the ablation result by comparing the determination of the percentage decrease to clinical statistical data of patients who have undergone ablation therapy; and
 outputting a graphical representation of the comparison and the validation of the ablation result.

2. The method of claim 1, wherein the first and second imaging data comprise diffusion tensor imaging (DTI) data.

3. The method of claim 2, further comprising:
 co-registering the MR data and the DTI data of the first imaging data; and
 co-registering the MR data and the DTI data of the second imaging data.

4. The method of claim 1, wherein the first imaging data is obtained before the ablation of the anatomy in the patient's brain has begun and the second imaging data is obtained after the ablation of the anatomy in the patient's brain has ended.

5. The method of claim 1, wherein outputting the graphical representation comprises outputting to a display the second fiber tracts along with the MR data of the patient's brain.

6. The method of claim 1, wherein the MR data comprise T1 weighted magnetic resonance (T1W MR) data of the patient's brain.

7. The method of claim 1, wherein the anatomy in the patient's brain comprises an amygdalohippocampal complex, an amygdala, a hippocampus, a lesion, or a tumor in the patient's brain.

8. A system for validating an ablation result in a patient's brain, comprising:
 a computing device in communication with a magnetic resonance imaging (MRI) device, the computing device configured to:
  receive magnetic resonance (MR) data of the patient's brain;
  receive first imaging data of the patient's brain;
  generate a segmented model of the patient's brain from the MR data, based on a 3D shape constrained deformable brain model adapted to the patient's brain, the 3D shape constrained deformable brain model comprising plate-like segments corresponding to boundaries of anatomy of the patient's brain;
  track, based on the first imaging data and the MR data, first fiber tracts passing through an anatomy in the patient's brain, wherein one of the plate-like segments of the segmented model of the patient's brain seeds the tracking of the first fiber tracts;

receive, from the MRI device, second imaging data of the patient's brain after ablation of the anatomy in the patient's brain has started;

track, based on the second imaging data and the MR data, second fiber tracts passing through the anatomy in the patient's brain, wherein the segment of the segmented model of the patient's brain seeds the tracking of the second fiber tracts;

determine a percentage decrease based on a comparison of one of (i) a first number of the first fiber tracts and a second number of the second fiber tract or (ii) a first volume occupied by the first fiber tracts and a second volume occupied by the second fiber tracts;

validate the ablation result by comparing the determination of the percentage decrease to clinical statistical data of patients who have undergone ablation therapy; and output, to a display in communication with the computing device, a graphical representation of the comparison and the validation of the ablation result.

9. The system of claim 8, wherein the first and second imaging data comprise diffusion tensor imaging (DTI) data.

10. The system of claim 8, further comprising the MRI device and the display.

11. The system of claim 8, wherein the computing device is further configured to:
co-register the MR data and the DTI data of the first imaging data; and
co-register the MR data and the DTI data of the second imaging data.

12. The system of claim 8, wherein the first imaging data is obtained before the ablation of the anatomy in the patient's brain has begun and the computing device is configured to obtain the second imaging data after the ablation of the anatomy in the patient's brain has ended.

13. The system of claim 8, wherein the computing device is further configured to output to the display the second fiber tracts along with the MR data of the patient's brain.

14. The system of claim 8, wherein the MR data comprise T1 weighted magnetic resonance (T1W MR) data of the patient's brain.

15. The system of claim 8, wherein the anatomy of in the patient's brain comprises an amygdalohippocampal complex, an amygdala, a hippocampus, a lesion, or a tumor in the patient's brain.

16. A non-transitory computer readable medium storing instructions for validating an ablation result in a patient's brain that, when executed by one or more processors, cause the one or more processors to:

receive magnetic resonance (MR) data of a patient's brain;

receive first imaging data of the patient's brain;

generate a segmented model of the patient's brain from the MR data, based on a 3D shape constrained deformable brain model adapted to the patient's brain, the 3D shape constrained deformable brain model comprising plate-like segments corresponding to boundaries of anatomy of the patient's brain;

track, based on the first imaging data and the MR data, first fiber tracts passing through an anatomy in the patient's brain, wherein one of the plate-like segments of the segmented model of the patient's brain seeds the tracking of the first fiber tracts;

receive, from a MRI device, second imaging data of the patient's brain after ablation of the anatomy in the patient's brain has started;

track, based on the second imaging data and the MR data, second fiber tracts passing through the anatomy in the patient's brain, wherein the segment of the segmented model of the patient's brain seeds the tracking of the second fiber tracts;

determine a percentage decrease based on a comparison of one of (i) a first number of the first fiber tracts and a second number of the second fiber tract or (ii) a first volume occupied by the first fiber tracts and a second volume occupied by the second fiber tracts;

validate the ablation result by comparing the determination of the percentage decrease to clinical statistical data of patients who have undergone ablation therapy; and output, to a display in communication with the computing device, a graphical representation of the comparison and the validation of the ablation result.

17. The non-transitory computer readable medium of claim 16, wherein the first and second imaging data comprise diffusion tensor imaging (DTI) data.

18. The non-transitory computer readable medium of claim 16, wherein the instructions further cause the one or more processors to:
co-register the MR data and the DTI data of the first imaging data; and
co-register the MR data and the DTI data of the second imaging data.

* * * * *